United States Patent [19]
Kristbjarnarson

[11] Patent Number: 6,049,730
[45] Date of Patent: Apr. 11, 2000

[54] METHOD AND APPARATUS FOR IMPROVING THE ACCURACY OF INTERPRETATION OF ECG-SIGNALS

[75] Inventor: Helgi Kristbjarnarson, Reykjavik, Iceland

[73] Assignee: Flaga hf, Reykjavik, Iceland

[21] Appl. No.: 09/221,169

[22] Filed: Dec. 28, 1998

[51] Int. Cl.[7] ................................................ A61B 5/04
[52] U.S. Cl. ................................................ 600/509
[58] Field of Search .............................. 607/508, 509, 607/516, 517, 512, 523

[56] References Cited

U.S. PATENT DOCUMENTS

| | | |
|---|---|---|
| 4,202,350 | 5/1980 | Walton . |
| 4,409,983 | 10/1983 | Albert . |
| 4,830,021 | 5/1989 | Thornton . |
| 5,010,893 | 4/1991 | Sholder . |
| 5,025,791 | 6/1991 | Niwa . |
| 5,036,856 | 8/1991 | Thornton . |
| 5,125,412 | 6/1992 | Thornton . |
| 5,197,489 | 3/1993 | Conlan . |
| 5,226,417 | 7/1993 | Swedlow et al. . |
| 5,233,984 | 8/1993 | Thompson . |
| 5,263,491 | 11/1993 | Thornton . |
| 5,265,619 | 11/1993 | Comby et al. . |
| 5,280,791 | 1/1994 | Lavie . |
| 5,333,615 | 8/1994 | Craelius et al. . |
| 5,348,008 | 9/1994 | Bornn et al. . |
| 5,368,026 | 11/1994 | Swedlow et al. . |
| 5,505,199 | 4/1996 | Kim . |
| 5,515,858 | 5/1996 | Myllymäki . |
| 5,573,013 | 11/1996 | Conlan . |
| 5,588,425 | 12/1996 | Sackner et al. . |
| 5,662,106 | 9/1997 | Swedlow et al. . |
| 5,670,944 | 9/1997 | Myllymäki . |
| 5,776,077 | 7/1998 | Kitazawa et al. . |

FOREIGN PATENT DOCUMENTS 0 467 507 A1  1/1992  European Pat. Off. .

*Primary Examiner*—Scott M. Getzow
*Attorney, Agent, or Firm*—Pillsbury Madison & Sutro

[57] ABSTRACT

An electrocardiographic measurement system, method and device uses a device such as an inclinometer, which measures the body position in three orthogonal planes x, y and z in order to correct the calculated vector for changes in ECG parameters, especially S–T segment level during ischemic attacks. Recordings are made with a sixteen channel recorder for twenty four hours and so it is necessary to have a measure of the posture of the subject to interpret the ECG. An inclinometer, which measures gravitational acceleration in all planes to the nearest degree is used, giving three traces for the three planes x, y and z. By initial calibration of the ECG changes due to body position or continuous running average the calculated vector of the ECG can be corrected by standard geometric methods.

23 Claims, 5 Drawing Sheets

METHOD AND APPARATUS FOR IMPROVING THE ACCURACY OF INTERPRETATION OF ECG-SIGNALS

FIELD OF THE INVENTION

This invention relates to electrocardiographic measurements, and, more particularly, to improving the accuracy of such measurements by taking into account dynamic and gravitational effects.

BACKGROUND OF THE INVENTION

An electrocardiogram ("ECG" or "EKG") is a graphic representation of the electrical activity generated by the heart during the cardiac cycle and is recorded from the body surface. Electrocardiography is described in Greenfield, J. C., Jr. "Electrocardiography," in *Cecil Textbook of Medicine*, Volume 1, 19th Ed., edited by Wyngaarden, J. et al., pp. 170–175, which pages are hereby incorporated herein by reference.

Vectorcardiography ("VCG") is a variant of electrocardiography ("ECG") dating back more than half a century. In 1946 Burger et al described the summation of electrocardiographic impulses into vectors in three orthogonal planes X, Y and Z. *Heart-Vector And Leads.* Br Heart J 1946;8:15714 163, which is incorporated herein by reference. Ten years later, Ernst Frank presented the lead system on which modern vectorcardiographic monitoring is based. *Accurate, clinically practical system for spatial vectorcardiography. Circulation,* 1956;13:737–744, which is incorporated herein by reference. In the early 1960's various authors described the use of vectorcardiograms in the diagnosis of acute myocardial infarction. Wolff et al, *Vectorcardiographic diagnosis: a correlation with autopsy findings in 167 cases. Circulation* 1961;23:861–880; Hoffman et al *Vectorcardiographic residua of inferior infarction: seventy-eight cases studied with the Frank system.* Circulation 1964;29:562–576; and Young et al *The frontal plane vectorcardiogram in old inferior myocardial infarction: criteria for diagnosis and electrocardiographic correlation.* Circulation 1968;37:604–623, each of which are incorporated herein by reference.

Continuous vectorcardiographic monitoring was first described in Hodges et al *Continuous recording of the vectorcardiogram in acutely ill patients.* Am Heart J 1974;88:593–595, which is incorporated herein by reference. This method was later used in several studies by Sederholm and co-workers who found a correlation between the evolution of QRS changes and the release of myoglobin and creatin kinase due to injury to the heart muscle. Similar relationships were found between the duration of ST vector magnitude changes and enzymatic release and chest pain.

Further development of continuous online VCG monitoring was made by Martin Riha at Östra Hospital Göteborg in collaboration with the Calmers Institute of Technology and Ortivus Medical AB. This resulted in the MIDA system (Myocardial Infarction Dynamic Analysis, Ortivus Medical, Täby, Sweden) which was introduced for clinical use as a tool for continuous on-line vectorcardiographic monitoring of ischaemia in 1986.

An ECG signal is a reflection of the electrical activity of the heart. The ECG signal differs, depending upon the placement of electrodes on the body, but generally it can be understood as a representation of a vector moving within the heart and seen from different angles in three-dimensional space, for example, as shown in FIG. 1A. The electrical vector of each part of the electrical process is the sum of all the electrical charge movements at a given moment in time. The mean QRS vector is shown in FIG. 1B. The different parts of the electrical process are denoted with the letters P, Q, R, S, T and U (FIG. 2). The first part of the electrical process represents electrical activity in the atria and is called P-wave. The Q, R and S portions of the wave are generally considered to represent the depolarization of the ventricle muscle, while the T-wave may represent repolarization of the muscle and inversion of the T-wave can signal ischaemia of the heart.

The level of the line connecting the S and T waves is called the S–T segment and deviation of that level from the normal baseline (isoelectric line), for example, as shown in FIG. 3, is generally considered to represent ischemia or injury of the heart muscle. Generally, inversion of the T-wave and depression of the S–T segment (as shown, for example, by the waves in FIGS. 4A and 4B, respectively) may represent cardiac muscle ischemia and injury. The more the S–T segment deviates from the baseline, the more severe the ischemia is considered. However, as with all parts of the electrical process in the heart, the S–T level looks different from the different electrodes of the ECG, as the electrical vector's relative position (magnitude) is different with respect to each electrode. In order to obtain a consistent measure of the level of the S–T segment it is therefore better to use the length of the electrical vector during this part of the process.

A major drawback of ECG systems is that the heart is connected to the body in a manner which permits limited movement. Thus, the heart changes its position within the thorax when people change their posture. As a result, an ECG can only be interpreted accurately if the subject is still during the recording, usually lying in a supine position.

Systems have been developed to allow simultaneous measurement of ECG signals and other signals which reflect movement of different parts of the body. For example, systems, e.g., as shown in U.S. Pat. No. 4,817,628 and International App. Patent PCT/FI95/00425, use accelerometers to correlate the movement of the subject with his ECG. The aim of these systems is to study and monitor the subject's movement and to then correlate such movement with the anomalous ECG readings. These systems require analysis of an ECG to determine whether anomalous signals are the result of disease or movement of the subject.

U.S. Pat. No. 4,993,421 discloses a cardiac monitoring system that generates ECG signals, and that employs an accelerometer to detect the activities of the subject. The monitoring system correlates changes in the ECG with changes in the physical activities of the subject to enable a physician to determine how physical activities effect the subject's ECG. However, the device disclosed in this patent does not provide any mechanism for correcting normal changes in ECG based upon the position or posture of the subject.

SUMMARY OF THE INVENTION

It is desirable to provide an ECG measurement system that takes into account gravitational effects associated with movement and/or changes in the position or posture of the subject.

It is also desirable to provide a ECG measurement system that allows for continuous measurement without requiring a practitioner to correlate the ECG with movement by the subject or with gravitational effects.

In one aspect, this invention is an electrocardiographic measurement system, method and device that employs an inclinometer, which measures the body position in three orthogonal planes x, y and z in order to correct the calculated vector for changes in ECG parameters, especially S–T segment level during ischemic attacks. A preferred use of the invention is to make recordings with a sixteen channel recorder for twenty four hours. The inclinometer measures the posture of the subject to interpret the ECG. The inclinometer, which measures gravitational acceleration in all planes to the nearest degree, gives three traces for the three planes x, y and z. By initial calibration of the ECG changes due to body position, or continuous running average, the calculated vector of the ECG can be corrected by standard geometric methods.

In one aspect, this invention is an electrocardiographic method comprising: determining an ECG signal for a subject; determining the position of the subject; and then adjusting the ECG signal based on the determined subject's position.

Preferably the inclinometer comprises three orthogonal position sensors connected to the subject in such a manner and location on the subject's torso so that the inclinometer housing moves in the same way as the subject's thorax or rib-cage, e.g., the sensors are preferably applied to the subject's sternum. In some embodiments, the adjusting comprises determining a correction factor based on the determined position; and then subtracting the correction factor from the determined ECG. The determining of the correction factor may comprise: providing a database mapping predetermined positions to predetermined correction factors; matching the determined position to a predetermined position in the database; and extracting from the database the predetermined correction factor corresponding to the predetermined position. The matching may be performed by one of estimation and interpolation. Preferably, the database contains between 50 and 100 entries.

In another aspect, this invention is an electrocardiographic method comprising: attaching an inclinometer to a subject in order to determine the position of the subject's rib cage with reference to the earth's gravitational field; providing a digital recorder capable of continuously recording the subject's ECG measurements and of simultaneously continuously recording signals from the inclinometer; placing on the subject electrodes connected to the recorder; continuously recording the subject's ECG measurements from the electrodes and simultaneously continuously recording signals from the inclinometer. Preferably the signals are continuously recorded for a period of between 12 and 24 hours. Preferably, the signals are stored in a memory whose storing frequency is 100 samples per second or more, but may be as low as 1 sample per 15 seconds. In preferred embodiments, the inclinometer comprises accelerometers having three orthogonal axes sensitive to the earth's gravitational force, and wherein (a) each signal from the three movements along the three orthogonal axes is separately stored; or (b) one signal is separately stored and two signals are stored as a sum signal of the two signals; or (c) all three signals are stored as a sum signal of the three signals. The recorded ECG measurements are then based on the corresponding recorded signals from the inclinometer.

In yet another aspect, this invention is an apparatus for simultaneous recording of electrocardiograph signals and position signals of a subject. The apparatus comprises an inclinometer; a first group of input channels for recording electrocardiograph signals so as to accurately determining the vector axis of the electrical activity of the heart; and a second group of input channels for storing position signals from an inclinometer. The apparatus also has a memory for storing the recorded electrocardiographic signals and the recorded position signals. Preferably the first group of input channels comprises 13 input channels and wherein the second group of input channels comprises 3 input channels. The inclinometer may have three accelerometric position sensors and the apparatus has three input channels to store signals from the three accelerometers.

The apparatus preferably stores the position data in different ways: (a) Each signal from the three movements along the three orthogonal axes is separately stored; or (b) one signal is separately stored and two signals are stored as a sum signal of the two signals; or (c) all three signals are stored as a sum signal of the three signals.

Again, it is preferred that storing frequency of the memory be about 100 samples per second or more, but may be as low as 1 sample per 15 seconds. The apparatus also has means for adjusting the recorded electrocardiographic signals based on the recorded position signals.

In yet another aspect, this invention is an electrocardiographic system having a memory and a processor. The memory stores ECG signals and corresponding position signals. The processor is programmed to: obtain an ECG signal and a corresponding position signal from the memory; determine an ECG vector corresponding to the obtained ECG signal; determine a position vector from the obtained corresponding position signal; determine a correction vector corresponding to the position vector; and adjust the ECG vector based on the determined ECG vector and the correction vector.

The system may also have a database mapping predetermined positions to predetermined correction factors and the processor may be programmed to determine the correction vector by matching the determined position to a predetermined position in the database; and then extracting from the database the predetermined correction factor corresponding to the predetermined position.

In yet another aspect, this invention is an ECG method for improving the accuracy of measured ECG signals of a subject. The method comprises: calibrating a database to store ECG signal correction factors by determining a standard ECG signal and a standard body position corresponding thereto based upon an ECG measurement and body position measurement taken when the subject is in a standard position, and variant ECG signals and variant body position measurements corresponding thereto based upon ECG measurements and body position measurements taken when the subject is in positions other than the standard position; determining a current ECG signal for the subject; determining a current body position of the subject; and using the stored ECG correction factors in the database to adjust the current ECG signal based upon the current body position of the subject.

BRIEF DESCRIPTION OF THE DRAWINGS

The above and other objects and advantages of the invention will be apparent upon consideration of the following detailed description, taken in conjunction with the accompanying drawings, in which the reference characters refer to like parts throughout and in which.

DETAILED DESCRIPTION OF THE PRESENTLY PREFERRED EXEMPLARY EMBODIMENTS

Structural Overview

Figure 1A:
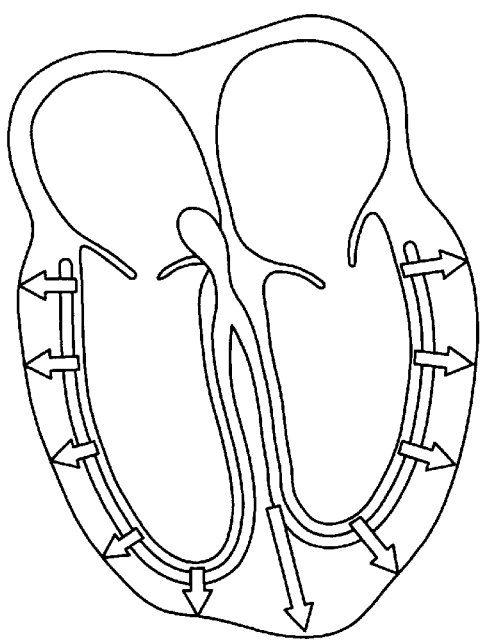
FIG. 1A shows a representation of electrical vectors within the heart.
Figure 1B:
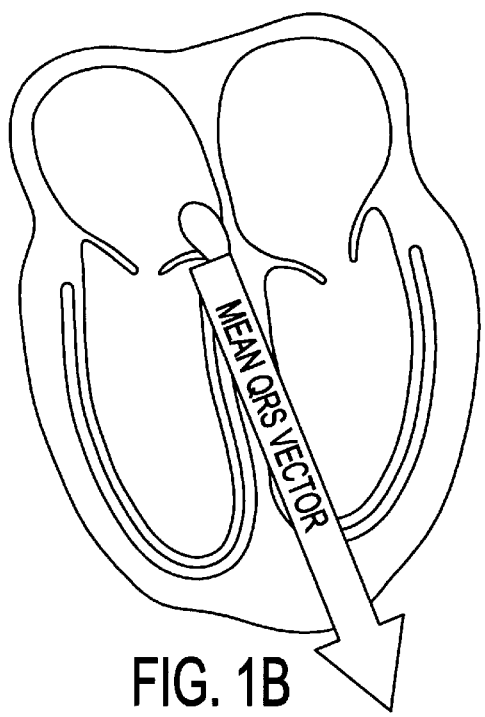
FIG. 1B shows a mean QRS vector of the heart.
Figure 2:
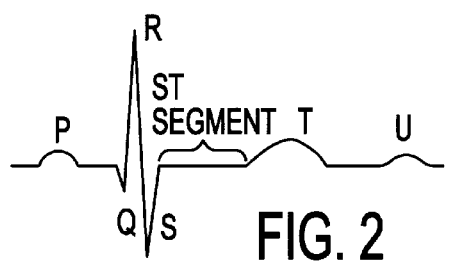
FIG. 2 shows an example of an ECG waveform.
Figure 3:
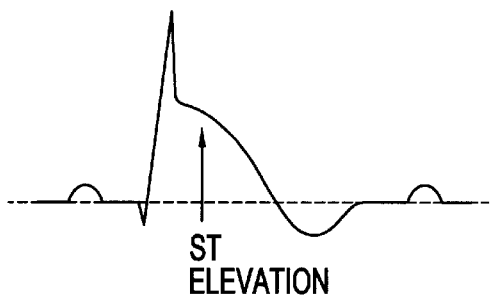
FIGS. 3, 4A and 4B show examples of ECG waveforms depicting possible cardiac injury.
Figure 4A:
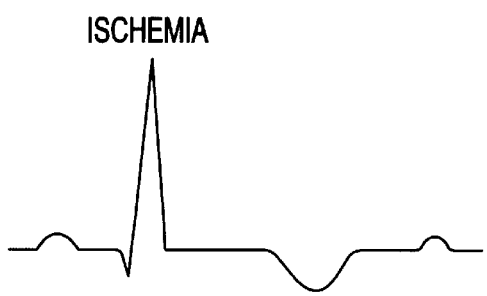
Figure 4B:
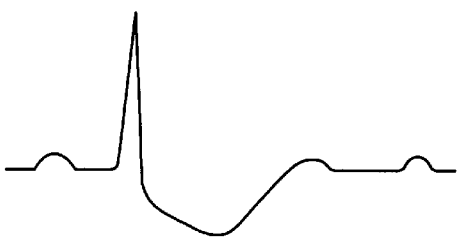
Figure 5:
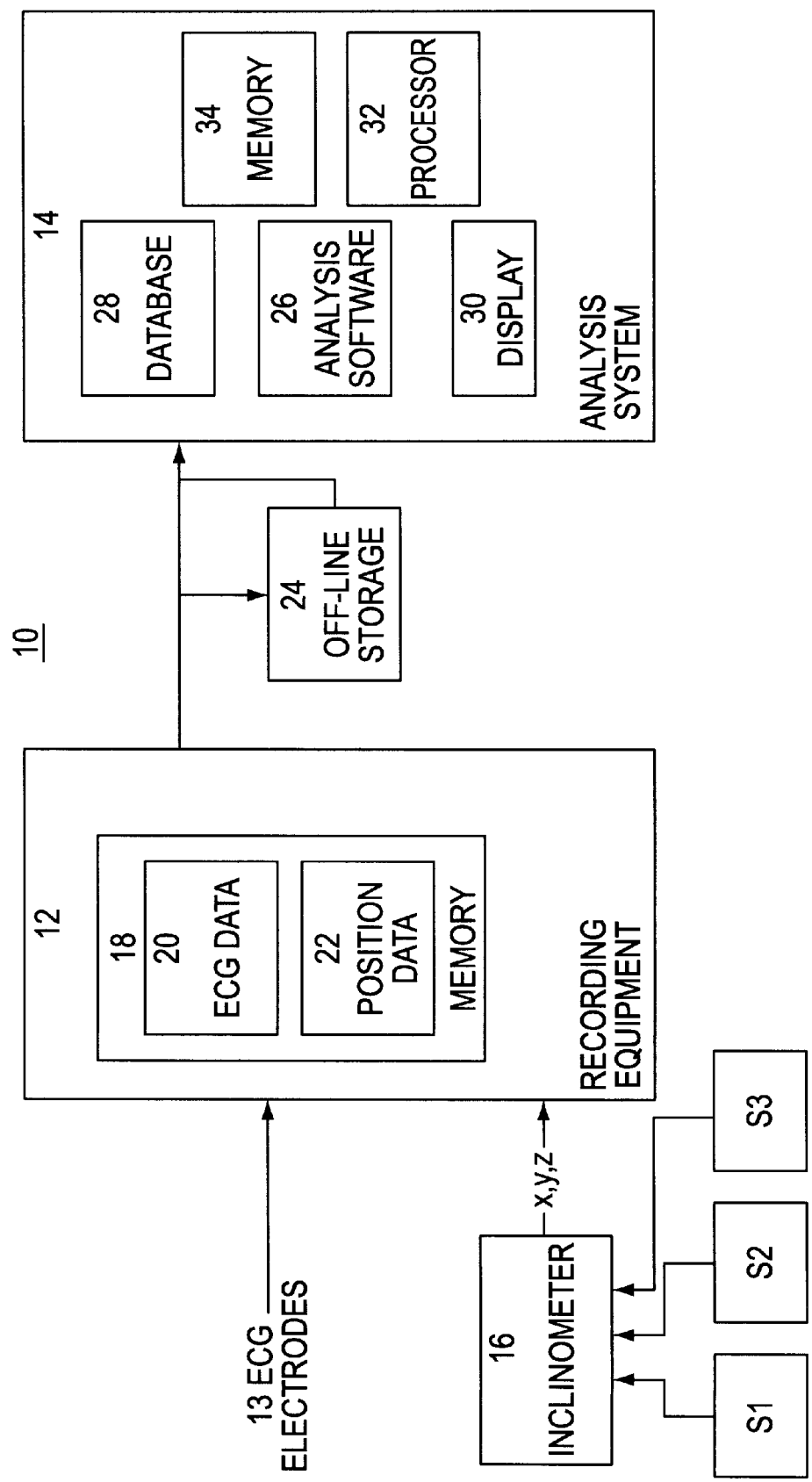
FIG. 5 shows a preferred embodiment of the structure of this invention.

As shown in FIG. 5, an ECG system 10 according to a preferred embodiment of this invention includes recording equipment 12 and an analysis system 14. The recording equipment 12 is made up of a sixteen channel digital recorder capable of continuously recording ECG measurements from up to thirteen of the sixteen electrodes (the thirteen electrodes denoted as ECG electrodes) for a period of time, preferably twenty-four hours or more. The system 10 also includes an inclinometer 16. The recorder 12 is capable of continuously recording the posture, position, or acceleration of the human torso (and particularly the rib cage) from the other three of the sixteen channels signals from the inclinometer 16. The terms "posture" and "position" are synonomous as used herein. Basically, these terms refer to the relative orientation of the human torso, and particularly the rib cage, relative to the gravitational field of the earth, which, when determined, can be used to approximate the relative orientation of the heart within the rib cage.

It can be appreciated that acceleration of the human torso or rib cage (e.g., during exercise) may also effect the relative orientation of the heart within the rib cage, and that these changes in the relative orientation of the heart will also be detected by the inclinometer 16. This is desirable, because the relative orientation of the heart within the rib cage will have an effect on ECG, irrespective of whether the change in relative orientation of the heart comes about by acceleration or by change in position.

Preferably the inclinometer 16 is made up of three orthogonal position sensors (S1, S2, S3), which are applied preferably to the sternum of a subject's torso (e.g., by being strapped by a harness) or to other part of the subject's torso which is likely to move in the same way as the case or rib-cage surrounding the heart. The inclinometer 16 comprises accelerometers sensitive in three orthogonal planes to the gravitational field of the earth. The inclinometer 16 is preferably a single unit casing holding the three position sensors or accelerometers.

Preferably, a standard, commercially available, sixteen channel recorder 12 is used. As noted above, because three of the channels are used for the inclinometer, thirteen channels are left for determining the ECG vector data. It will be appreciated by those skilled in the art, however, that only nine channels or electrodes are required for performing a twelve-lead ECG measurement, and that only eight channels or electrodes are required for using the standard Frank leads. Thus, the present invention need not provide sixteen channels, as a total of only eleven channels are needed for the device when using the Frank leads (eight channels for the Frank leads and three channels for the inclinometer), and that only nine channels are needed for the device when using the standard twelve-leads (nine channels for the twelve leads and three channels for the inclinometer). It is also known that the Frank leads (A, C, E, I, M, H, F, and Ref) can be used to mathematically derive the twelve-leads, and vice-versa.

In accordance with another aspect of the present invention, the device of the present invention is flexible in that the thirteen available channels can be used to obtain both the Frank leads and the standard twelve leads. This can be done by sharing the following electrodes $V_4$ with the Frank C, $V_6$ with the Frank A, RL with the Frank Reference Electrode, and LL with the Frank F (See FIG. 8). In this manner, both the 12-lead ECG and the Frank lead ECG can be determined directly, and at the same time if desired.

Of course, only one set of ECG electrodes (either the Frank leads or the 12 lead electrodes—the 12 lead electrodes being preferred) is required. In the event that only one set of ECG electrodes are provided, it may nevertheless be desirable (although not essential) to utilize a recorder having sixteen channels. In this manner, the additional channels can be used to record other signals, such as oximetry, microphone (fonocardiogram), respiratory effort sensor, or EEG signals.

The recording equipment 12 includes a memory 18 capable of storing ECG data 20 and position data 22. Preferably the memory 18 can store at least twenty-four hours worth of ECG data 20 and corresponding position data 22. The memory 18 is digital or an analog device memory whose storing frequency is preferably one hundred samples per second or more, but may be as low as one sample per fifteen seconds. The signals from the inclinometer 16 are preferably stored (as position data 22) with a sampling rate of 100 Hz for each of the three orthogonal channels, although several variants may be made of this by using faster or slower sampling rates, and in some instances two or all three channels may be combined to save storage memory.

The recording equipment 12 is connectable either to an external, off-line storage 24 or directly to the analysis system 14. The analysis system 14 is also capable of obtaining data directly from the off-line external storage 24. In another contemplated embodiment, the correction vector data is displayed continuously on-line as it is recorded.

The analysis system 14 includes analysis software 26 and a database 28. The database 28 is used by the analysis software 26 to determine ECG correction factors, as described below. The database 28 contains a mapping from three-dimensional co-ordinates to correction factors. Preferably the database 28 stores mappings between 50 to 100 positions in three-dimensional space.

The analysis system 14 can be implemented on any general purpose or special purpose computer having a processor 32 and a memory 34. The analysis software can be written in any programming language to run on the computer of the system 14.

Operational Overview

Preferably, the ECG system 10 of this invention is used for ambulatory assessment of signs of ischemic changes in the ECG signals. This invention is used to diagnose the ischemic changes in the ECG during different activities of a subject, preferably during a twenty-four hour time period. Lschemia is diagnosed by the level of the S–T segments of the ECG. As noted earlier, when the S–T segment in a standard twelve-lead ECG is elevated from the baseline of the ECG signal, this represents possible ischemia or cardiac injury. The heart changes position within the ribcage with changes of the human body posture, position, or acceleration. The level of the S–T segment generated by the ECG signal is dependent on the electrode studied and the relative position of the heart. The most accurate estimate of the S–T level is done by calculating the vector of electrical activity by a method originally described by Frank.

In use, a subject (i.e., a patient) carries the recording equipment 12 with the thirteen ECG electrodes connected to the subject's body in the appropriate manner, e.g., the thirteen electrodes are placed in the standard twelve-lead ECG electrode placements and the Frank lead locations (as described in Circulation 1956; 13:737–744, mentioned above). The recording equipment 12 then continuously records the subject's ECG measurements from the thirteen ECG electrodes for a period of preferably about twenty-four hours. At the same time, the recording equipment 12 also continuously records from the other three channels (x, y, z) signals from the inclinometer 16 made up of the three orthogonal position sensors (S1, S2, S3) which have been applied to the subject's sternum.

As noted, the inclinometer 16 is preferably mounted on the subject's sternum for movement corresponding to the movement of the subject's sternum as the subject changes position, posture, etc. The inclinometer 16 should be attached to the subject in such a way as to allow that signals from the accelerometers to be used to estimate changes in the position of the heart within the subject's rib-cage.

The changes in the heart's position, as reflected in the total change in the vectors of the ECG, are related to the changes in position as measured by the position sensors.

Recall that the database 28 contains a mapping from three-dimensional co-ordinates to correction factors. Initially the database 28 must be calibrated to store the correction factors for each particular subject when the subject is seemingly healthy (e.g., seemingly presenting a normal ECG and no chest pain or angina pectoris). In order to perform this calibration, a standard position (for example, supine) is chosen. In this calibration procedure, the inclinometer 16 is used to gather information about the subject's body posture to estimate the change of position of the heart within the thorax to account for possible changes in the electrical vector of the heart. It is best to do this by calibrating the system prior to the beginning of the recording, for example, by having the subject assume the selected standard position, e.g., lying supine, and then moving slowly into several different positions. Then, the changes in the electrical vectors of the ECG are calculated, and related to the associated body positions of the subject determined by the inclinometer 16. The correction value for each posture or position is found and used subsequently as a basis during the recording to correct the vector change as compared to the standard position.

The corrected vector gives a more reliable measure of pathological changes in S–T segments of the ECG due to ischemia or injury to the heart muscle during the recording period.

Once the system has been calibrated, ECG measurements and position measurements are made by the recording equipment 12. Later, when the measurements are to be displayed and reviewed, all recordings of the ambulatory ECG are recalculated as if they were made in the standard (i.e., the calibration) position.

Variants of this calibration approach include continuous self-calibration, as opposed to the pre-calibration approach. This is performed by monitoring QRS segments and assuming that changes in the vector for this signal reflect the heart's position, i.e., by assuming that the subject is healthy and that the changes in QRS are not related to cardiac injury or ischemia As such, the changes can be continuously correlated with the positions provided by the inclinometer 16 and can be stored in the database as correction values. Thus, the continuously measured changes can be used to calibrate the correction factor needed for a correct evaluation of changes in S–T level. When an ECG measurement then falls outside a predetermined range for a normal ECG measurement, this can be detected as ischemia or other cardiac injury.

Figure 6:
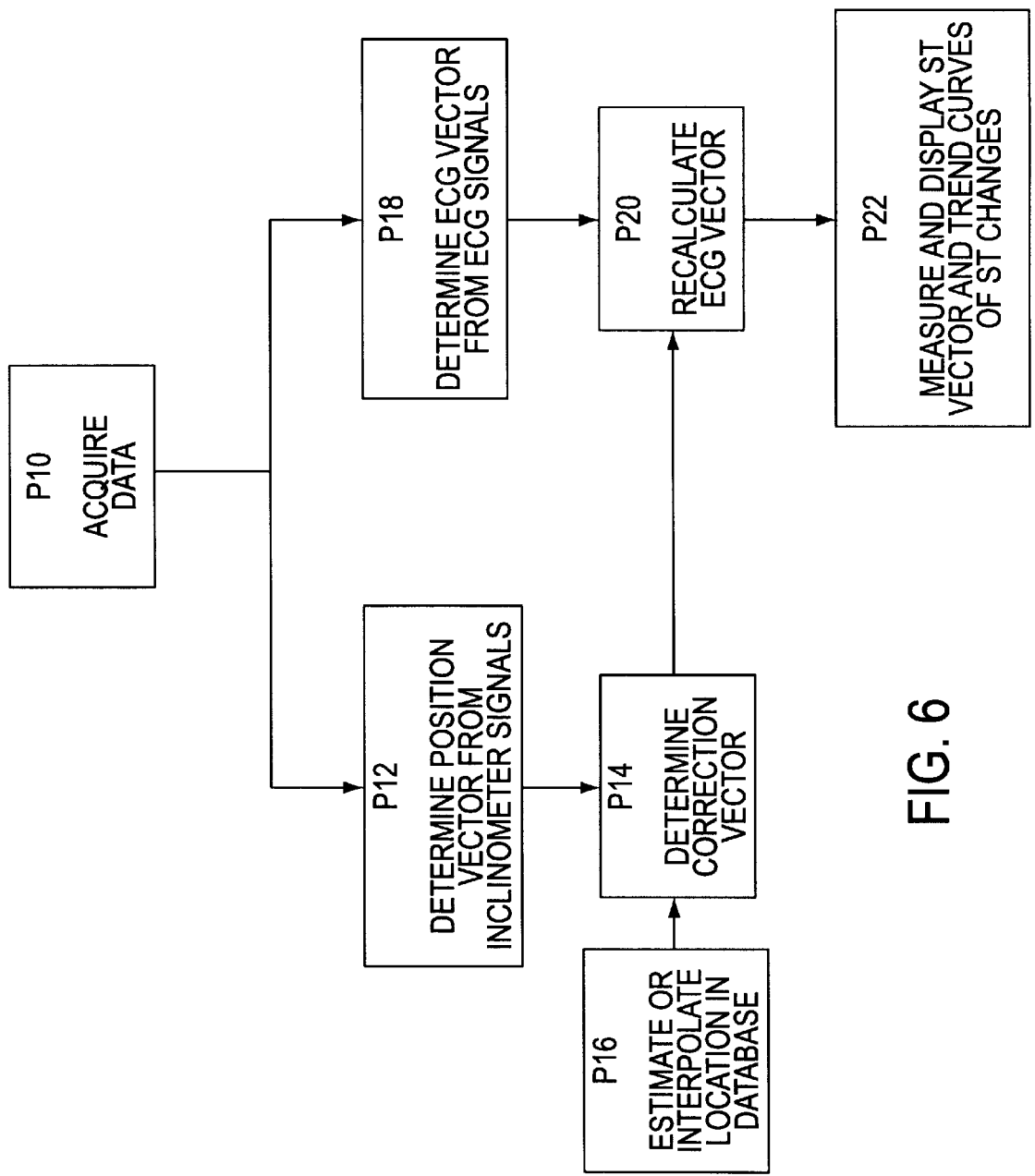
FIG. 6 is a flowchart showing the operation of this invention.

The process of analysis of acquired data is shown in FIG. 6. The data analysis is performed by the analysis software 26 on the analysis system 14. The system 14 may analyze data currently in the memory 18 of the recording equipment 12, or it may analyze data previously stored in off-line storage 24.

For each time period for which data was recorded, the analysis software 26 obtains the ECG data and the corresponding position data (at P10). For the position data, the analysis software 26 determines the position vector ($V_p$) (at P12). This position vector ($V_p$) is then used to determine (at P14) the correction vector ($V_c$). A vector $V_p'$ in the database 28 is found (by estimation or interpolation at P16) which most closely corresponds to the position vector $V_p$. Then, the correction vector $V_c$ corresponding to database vector $V_p'$ is selected as the correction vector.

At the same time, the ECG vector ($V_o$) is determined (at P18) from the ECG signals. A corrected ECG vector V' is calculated (at P20) based on the correction vector $V_c$ (determined at P14) and the ECG vector $V_o$ determined at P18.

The corrected ECG vector V' is then used to display the ST curves (at P22) on the display 30 of the analysis system 14.

Standard geometric methods are used to calculate the correction factor of the vector (at P20), i.e., standard methods of geometry are used to add and subtract vectors.

The correction vector: $\vec{V}_c = \langle x_c, y_c, z_c \rangle$ is estimated from the database. It reflects the correction of the measured ECG vector $\vec{V}_0 = \langle X_0, Y_0, Z_0 \rangle$ according to the measured position by the inclinometer. The corrected vector is then $$\vec{V}' = \vec{V}_0 - \vec{V}_c$$

calculated by means of the formula:

$$\|\vec{V}'\| = \sqrt{(x_0 - x_c)^2 + (y_0 - y_c)^2 + (z_0 - z_c)^2}$$

In this way, a more reliable value can be obtained for the changes in the S–T level due to ischemia. Thus, in operation, when the recording is reviewed, the analysis software 26 is used to calculate the S–T vector over time and the result is plotted as a graph on a display 30 of the analysis system 14. By selecting, e.g., by clicking, the S–T graph trace, a user can display the other ECG channels and visually verify that the suspected change in the S–T level is reflected in the normal ECG.

Figure 7B:
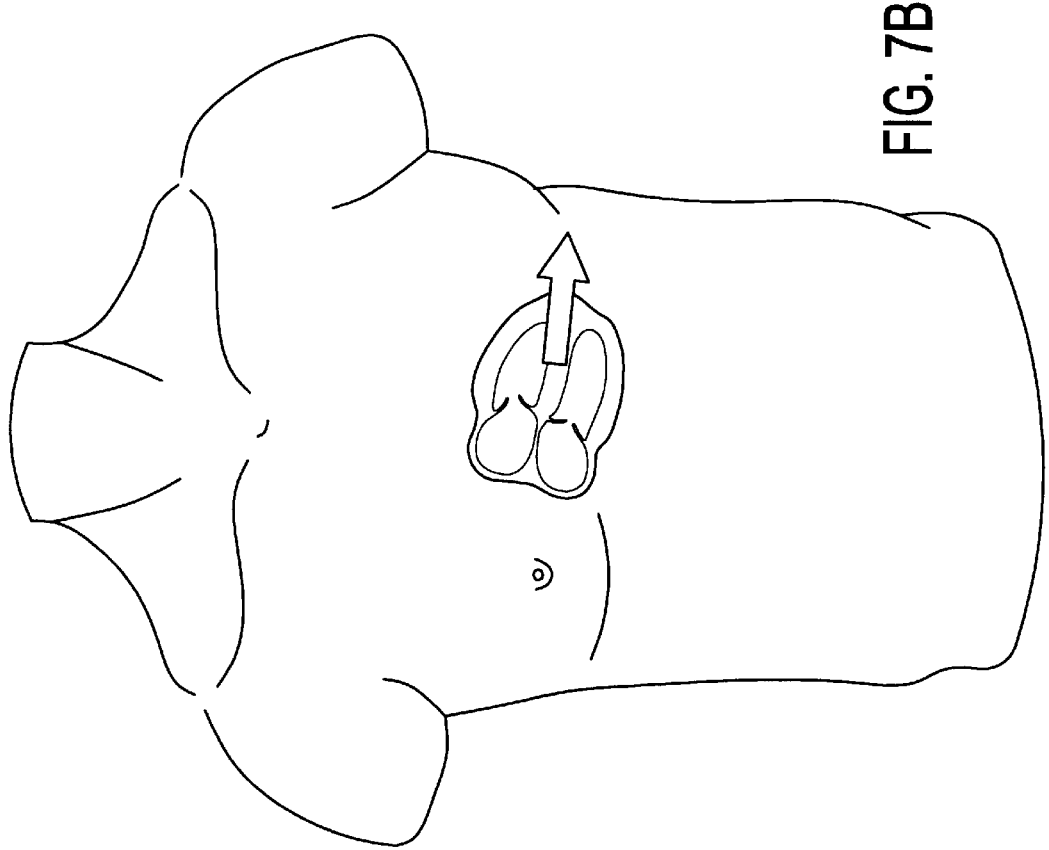
FIGS. 7A, 7B show that a change in the heart's position can change the direction of the electrical vector, although no change has occurred in the heart itself.
Figure 7A:
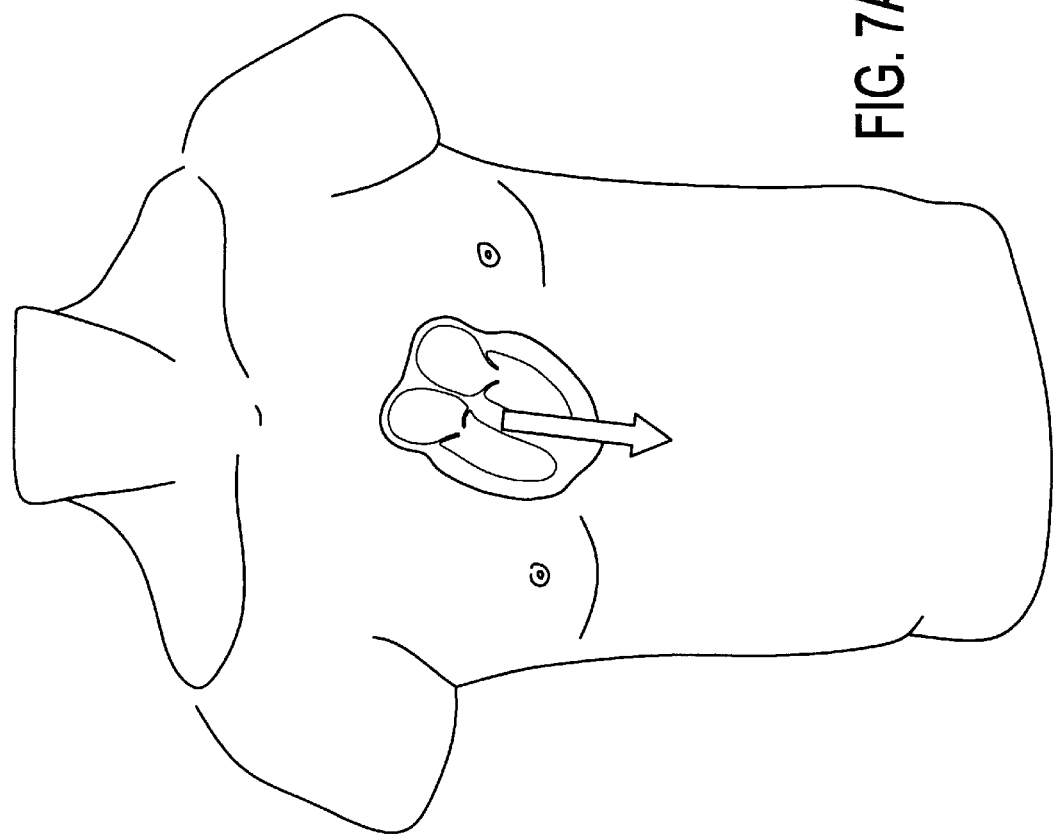

The calculations of the exact values of the vector are dependent on the assumption of no change in the spatial direction of the heart over time. However, since the heart moves as a restricted pendulum within the thorax, the length of the electrical vector may appear changed, due to its changed angle to the electrodes of the ECG (see FIGS. 7A and 7B which show that a change in the heart's position can change the direction of the electrical vector although no change has occurred in the heart itself).

Figure 8:
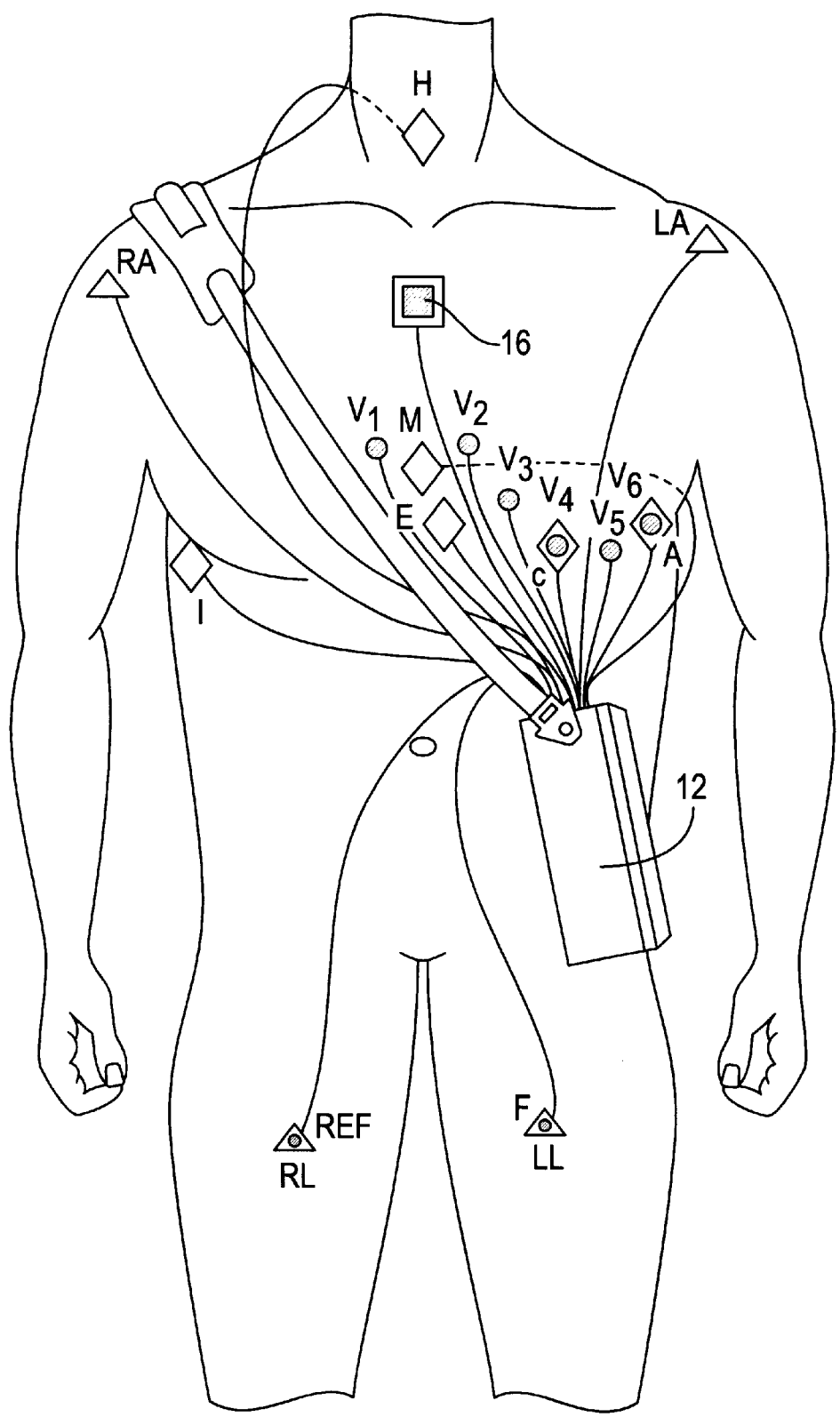
FIG. 8 is a perspective view of a subject wearing the device in accordance with a preferred embodiment of the present invention.

FIG. 8 is a perspective view of a subject wearing the device in accordance with a preferred embodiment of the present invention. In the embodiment shown, the subject is harnessed by nine electrodes connected to the recorder device 12, the electrodes including the six Wilson precordial electrodes $V_1, V_2, V_3, V_4, V_5, V_6$, the left arm electrode (LA), right arm electrode (RA), left leg electrode (LL), and the right leg electrode (RL). The software 26 of the present invention is programmed to select the combinations of electrodes of the nine provided which will produce the twelve leads I, II, III, AVR, AVL, AVF, $V_1, V_2, V_3, V_4, V_5, V_6$ for a 12-lead ECG.

While the electrodes are shown placed individually, e.g., as would be the case with adhesive electrodes, it should be appreciated that the electrodes can be mounted on an appropriate harness, as well known in the art.

As also shown, the inclinometer 16 is mounted on the sternum in fixed relation. Preferably, as shown, the three position sensors constituting the inclinometer are housed in a common casing. The casing can be fixed relative to the sternum adhesively (e.g., by medical adhesive tape) or by an appropriate harness. The harness that may be used for one or more of the nine electrodes can be the same harness used for the inclinometer.

The present invention is especially useful for monitoring the changes in S–T level and T wave inversion during cardiac ischemia Subjects with coronary artery disease often have pain during exercise called angina pectoris. This pain can be a symptom of insufficient oxygen supply to the cardiac muscle called ischemia. Ischemia may be present without pain and is then only diagnosable through changes in S–T level and T wave in the ECG signal.

This invention is also be useful for exact measurements of the electrical activity of the heart in other circumstances for example when studying the autonomic control of the heart and effects of changes in blood pressure. The invention relates to a method and equipment to make a long-term recording, sometimes 24 hrs or more usually under ambulatory conditions to estimate changes in the physiological or pathological condition of the heart. Since the heart changes its position inside the thorax during change in posture the electrical vector which expresses the condition of the heart muscle changes its position. The parameters used to estimate the condition of heart muscle such as S–T changes, are usually referred to a subject lying still in supine position and electrodes placed in a standardized way on the subjects body.

As used herein, the term "subject" or "patient" are used to denote the individual being measured by this method. It may be a healthy or a sick human being or even an animal.

As used herein, the term "ambulatory" denotes recording under conditions where the subject can move freely without being tied by cables to a stationary recording system. All the necessary recording equipment is sufficiently small and light so that the subject can easily carry it around during normal daily activities.

Thus are provided a method and a device for improving the accuracy of interpretation of ECG-signals. One skilled in the art will appreciate that the present invention can be practiced by other than the described embodiments, which are presented for purposes of illustration and not limitation, and the present invention is limited only by the claims that follow.

What is claimed:

1. An electrocardiographic ("ECG") method comprising:
   (A) determining an ECG signal for a subject;
   (B) determining the position of the subject; and
   (C) adjusting the ECG signal based on the determined subject's position.

2. A method as in claim 1 wherein the position of the subject is determined using an inclinometer comprising three orthogonal position sensors connected to the subject in such a manner and location as to move in the same was the subject's rib-cage.

3. A method as in claim 2 wherein the sensors are applied to the subject's sternum.

4. A method as in claim 1 wherein the adjusting comprises:
   determining a correction factor based on the determined position; and
   subtracting the correction factor from the determined ECG.

5. A method as in claim 4 wherein the determining of the correction factor comprises:
   providing a database mapping predetermined positions to predetermined correction factors;
   matching the determined position to a predetermined position in the database; and
   extracting from the database the predetermined correction factor corresponding to the predetermined position.

6. A method as in claim 5 wherein the matching is performed by one of estimation and interpolation.

7. A method as in claim 5 wherein the database contains between 50 and 100 entries.

8. A method as in claim 5 further comprising calibrating the database for the subject.

9. An electrocardiographic ("ECG") method comprising:
   attaching an inclinometer to a subject in order to determine the position of the subject's rib cage with reference to the earth's gravitational field;
   providing a digital recorder capable of continuously recording the subject's ECG measurements and of simultaneously continuously recording signals from the inclinometer;
   placing on the subject electrodes connected to the recorder;
   continuously recording the subject's ECG measurements from the electrodes and simultaneously continuously recording signals from the inclinometer.

10. A method as in claim 9 wherein the signals are continuously recorded for a period of between 12 and 24 hours.

11. A method as in claim 9 wherein in the signals are stored in a memory whose storing frequency is about 100 samples a second or more, but may be as low as 1 sample per 15 seconds.

12. A method as in claim 9 wherein the inclinometer comprises accelerometers comprising three orthogonal axes sensitive to the earth's gravitational force, and wherein (a) each signal from the three movements along the three orthogonal axes is separately stored; or (b) one signal is separately stored and two signals are stored as a sum signal of the two signals; or (c) all three signals are stored as a sum signal of the three signals.

13. A method as in claim 9 further comprising:
   adjusting the recorded ECG measurements based on the corresponding recorded signals from the inclinometer.

14. An apparatus for simultaneous recording of electrocardiograph signals and position signals of a subject, the apparatus comprising:
   an inclinometer;
   a first group of input channels for recording electrocardiograph signals so as to accurately determining the vector axis of the electrical activity of the heart;
   and a second group of input channels for storing position signals from the inclinometer;

a memory for simultaneously storing the recorded electrocardiographic signals and the corresponding recorded position signals.

15. An apparatus as in claim 14 wherein the first group of input channels comprises 13 input channels and wherein the second group of input channels comprises 3 input channels.

16. An apparatus as in claim 14 wherein the inclinometer comprises three accelerometric position sensors and wherein the apparatus comprises three input channels to store signals from the accelerometer.

17. An apparatus as in claim 16 wherein:

(a) each signal from the three movements along the three orthogonal axes is separately stored; or (b) one signal is separately stored and two signals are stored as a sum signal of the two signals; or (c) all three signals are stored as a sum signal of the three signals.

18. An apparatus as in claim 16 wherein a storing frequency of the memory is about 100 samples a second or more, but may be as low as 1 sampler per 15 seconds.

19. An apparatus as in claim 16 further comprising:

means for adjusting the recorded electrocardiographic signals based on the recorded position signals.

20. An electrocardiographic system comprising:

(A) memory storing ECG signals and corresponding position signals; and (B) a processor programmed to:

obtain an ECG signal and a corresponding position signal from the memory;

determine an ECG vector corresponding to the obtained ECG signal;

determine a position vector from the obtained corresponding position signal;

determine a correction vector corresponding to the position vector; and adjust the ECG vector based on the determined ECG vector and the correction vector.

21. A system as in claim 20 further comprising a database mapping predetermined positions to predetermined correction factors and wherein the processor is programmed to determine the correction vector by:

matching the determined position to a predetermined position in the database; and extracting from the database the predetermined correction factor corresponding to the predetermined position.

22. A system as in claim 21 wherein the adjusting comprises:

subtracting the correction factor from the determined ECG.

23. An electrocardiographic ("ECG") method for improving the accuracy of measured ECG signals of a subject, the method comprising:

calibrating a database to store ECG signal correction factors by determining a standard ECG signal and a standard body position corresponding thereto based upon an ECG measurement and body position measurement taken when the subject is in a standard position, and variant ECG signals and variant body position measurements corresponding thereto based upon ECG measurements and body position measurements taken when the subject is in positions other than the standard position;

determining a current ECG signal for the subject;

determining a current body position of the subject; and using the stored ECG correction factors in the database to adjust the current ECG signal based upon the current body position of the subject.

* * * * *